(12) United States Patent
Guo et al.

(10) Patent No.: US 8,962,647 B1
(45) Date of Patent: Feb. 24, 2015

(54) CONJUGATE OF POLYETHYLENE GYLCOL AND NALOXONE AND PHARMACEUTICAL COMPOSITION AND USE THEREOF

(71) Applicant: Jenkem Technology Co., Ltd. (Tianjin), Tianjin (CN)

(72) Inventors: Zhixiong Guo, Beijing (CN); Zewang Feng, Beijing (CN); Lihua Xu, Beijing (CN); Xuan Zhao, Beijing (CN)

(73) Assignee: Jenkem Technology Co., Ltd. (Tianjin), Tianjin (CN)

( * ) Notice: Subject to any disclaimer, the term of this patent is extended or adjusted under 35 U.S.C. 154(b) by 0 days.

(21) Appl. No.: 14/376,680

(22) PCT Filed: Feb. 21, 2013

(86) PCT No.: PCT/CN2013/000166
§ 371 (c)(1),
(2) Date: Aug. 5, 2014

(87) PCT Pub. No.: WO2013/123824
PCT Pub. Date: Aug. 29, 2013

(30) Foreign Application Priority Data

Feb. 22, 2012 (CN) .......................... 2012 1 0040133

(51) Int. Cl.
A61K 31/485 (2006.01)
C07D 489/04 (2006.01)
A61K 47/48 (2006.01)

(52) U.S. Cl.
CPC ......... *A61K 47/48215* (2013.01); *A61K 31/485* (2013.01)
USPC ........................................... 514/282; 546/44

(58) Field of Classification Search
USPC .............................................. 514/282; 546/44
See application file for complete search history.

(56) References Cited

U.S. PATENT DOCUMENTS 7,786,133 B2 * 8/2010 Bentley et al. ................. 514/282

FOREIGN PATENT DOCUMENTS

| CN | 1717209 A | 1/2006 |
|---|---|---|
| CN | 101805343 A | 8/2010 |
| CN | 102190719 A | 9/2011 |
| WO | WO 93/24476 A1 | 12/1993 |

OTHER PUBLICATIONS

International Search Report (in English) mailed on May 23, 2013 for PCT/CN2013/000166.
Written Opinion (in English) mailed on May 23, 2013 for PCT/CN2013/000166.

* cited by examiner

*Primary Examiner* — Charanjit Aulakh
(74) *Attorney, Agent, or Firm* — Swanson & Bratschun, L.L.C.

(57) ABSTRACT

Provided are a PEG-naloxone conjugate of general formula (II) and a pharmaceutical composition comprising the conjugate. In the conjugate, n is an integer in the range of 1-20. Also provided is a three-branched or four-branched conjugate of PEG and naloxone. Structural modification of naloxone with a hydrophilic polymer improves the pharmacokinetic properties of the drug, increase the water solubility of naloxone, improve the in vivo distribution of the drug, reduce the side effects of naloxone on central nervous system, and relieve bowel dysfunction and constipation caused by chronic administration of opioids. Also provided are a pharmaceutical composition comprising the conjugate of the invention and use of the conjugate.

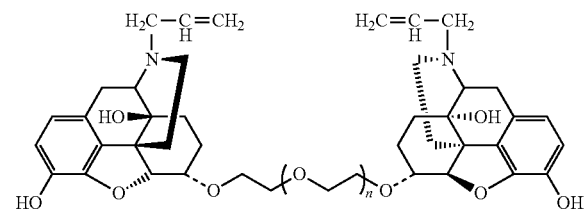

25 Claims, No Drawings

CONJUGATE OF POLYETHYLENE GYLCOL AND NALOXONE AND PHARMACEUTICAL COMPOSITION AND USE THEREOF

CROSS REFERENCE TO RELATED APPLICATIONS

This application is a National Stage Entry of International Application No. PCT/CN2013/000166 (WO 2013/123824), filed on Feb. 21, 2013, and claims the benefit of Chinese Application No. 201210040133.2, filed on Feb. 22, 2012, which is incorporated herein by reference in its entirety for all purposes as if fully set forth herein.

TECHNICAL FIELD

The present invention relates to a hydrophilic polymer-naloxone conjugate, in particular, a conjugate of a small molecular oligomeric ethylene glycol and naloxone, and to a pharmaceutical composition thereof.

BACKGROUND OF THE INVENTION

Opioid analgesics, such as morphine, are irreplaceable strong analgesics which have been widely used in clinical practice. Data shows that a total of 230 million prescriptions of opioids were written out just in the year 2007 in the US. Opioids mainly act on opioid receptors. Opioid receptors include three types, μ-, δ- and κ-receptors, each includes various subtypes. Opioid receptors exist in central nervous system such as spinal cord as well as peripheral nerves in stomach, small intestine, exocrine glands and the like. Therefore, opioid analgesics, having strong analgesic effects on central nervous system, lead to side effects by acting on peripheral opioid receptors. Primary side effects include opioid-induced bowel dysfunction and constipation. For patients suffering from chronic pain, in particular, these side effects always affect their quality of life due to chronic administration of opioids for pain relief.

Naloxone (structural formula I) is a derivative of oxymorphine, and is a specific antagonist of opioid receptors, having competitive antagonistic effects on various types of opioid receptors in vivo. It binds to opioid receptors in vivo to counteract excessive release of β-endorphins. The in vivo absorption and metabolism of naloxone are rapid; and the antagonistic effects thereof are strong. It can pass through blood-brain barrier easily, and bind to the receptors in place of morphine-like substances, thereby relieving CNS inhibition and recovering normal functions of organs such as brain, heart, and lungs rapidly without the occurrence of drug dependence, withdrawal symptoms and respiratory depression as in the case of morphine-like substances. Naloxone is a specific antidote for morphine overdose as well as a diagnostic agent for morphine and heroin addicts. Recent domestic and foreign clinical trials of naloxone for the treatment of acute intoxication of alcohol or diazepam, cerebral infarction, acute or chronic respiratory failure, and various severe shock have achieved good results as well. Since 2002, almost a hundred of production approval documents for naloxone have been issued by SFDA. During 2008 and 2009, a total of 18 manufacturers were providing naloxone products for four regions, namely Beijing, Zhejiang Province, Jilin Province and Yunnan Province in large amounts.

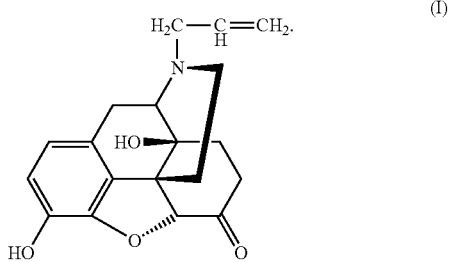

(I)

Although naloxone is an opioid receptor antagonist used most widely in clinic practice currently, it is inefficacious when administered orally in the form of tablets due to a significant first pass effect of hepar. Only two dosage forms, injections and sublingual tablets, are currently used in clinical practice. Meanwhile, due to significant penetration of naloxone through blood-brain barrier, it counteracts the analgesic effect of opioids while reducing the bowel dysfunction and constipation caused by chronic opioid administration in patients suffering from chronic pain.

The technology of polyethylene glycol (PEG) modification (hereinafter also referred to as PEGylation) is a new drug delivery technology developed rapidly in recent years and primarily for injection administration systems. It is a technology of linking activated PEG molecules to drug molecules or surfaces. PEGylated small molecular drugs mainly have the following advantages: (i). increased water solubility; (ii). reduced toxicity; (iii). increased circulating half-life of the drugs, reduced administration frequency, improved patient compliance, improved quality of life, and reduced treatment costs; (iv). reduced enzymolysis, and increased bioavailability; and (v). reduced penetration through blood-brain barrier, and reduced CNS side effects. Upon PEGylation of drugs, the pharmacokinetics of the drugs changes, and in turn, the pharmacodynamics thereof changes. In particular, PEG can prolong the duration in which the blood levels of the drugs are maintained at or close to target concentrations, thereby ensuring sufficient efficacy of the drugs. Currently, representative PEGylated pharmaceutical products in the international market include PEG-intron®, PEGasys®, Neulasta®, Macugen®, Neulasta®, and MICERA. So far, no PEGylated small molecular drugs have been approved for marketing in the international market, though several products, such as NKTE-102 and NKTR-118 from Nektar Therapeutics, have entered phase II or phase III clinical trials.

Our experimental group has been endeavored to researches of PEGylated small molecular drugs (related patents include Chinese Patent Nos. ZL03 8 01109.3, ZL 2004 1 0029615.3, ZL 2004 8 0005763.X, ZL 2008 1 0093688.7, ZL 02 1 07842.4, and ZL 02 1 08778.4). Our researches focus on linking PEG molecules to small molecular drugs, and the resulting products are significantly improved, having increased water solubility and reduced toxicity.

The product prepared by modifying naloxone structure with the technology of PEGylation, NKTR-118, entered phase III clinical trials (see http://www.nektar.com/pdf/pipeline/NKTR-118/pr__20110315.pdf). in March of 2011. In NKTR-118, PEG links to only one active moiety.

The object of the present invention is to overcome the defects of the existing technology, and solve the problem of conjugating multiple naloxone molecules to a single PEG molecule. In the present invention, the technology of PEGylation is employed for structural modification of naloxone, and by linking naloxone to PEG having low molecular weight, the pharmacokinetic properties of the drug are improved, the water solubility of naloxone is increased, the in vivo distribution of the drug is improved, the side effects of naloxone on CNS are reduced, the bowel dysfunction and constipation caused by chronic administration of opioids are alleviated, and injections and formulations for oral administration are developed. The experimental group, depending on its own advantages, synthesized and screened a number of PEG-naloxone derivatives. Unlike NKTR-118, in the compounds of the present invention, two or more active moieties are linked to a single PEG molecule. Therefore, the opioid receptor antagonistic activity of these compounds is superior to that of NKTR-118 of the same molecular weight.

SUMMARY OF THE INVENTION

The present invention provides a PEG-naloxone conjugate of general formula (II) or a pharmaceutically acceptable salt thereof:

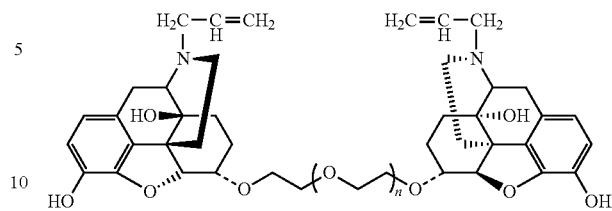

(II)

wherein n is an integer in the range of 1 to 20. Preferably, n is an integer in the range of 1 to 15. More preferably, n is an integer in the range of 2 to 15. Even more preferably, n is an integer in the range of 2 to 14, 3 to 13, or 4 to 12.

In some embodiments, the conjugate is in a configuration of (α,α), (β,β), (α,β), or a mixture thereof; and a preferred configuration is (α,α) or (β,β).

A further aspect of the present invention provides a PEG-naloxone conjugate of general formula (III) or a pharmaceutically acceptable salt thereof:

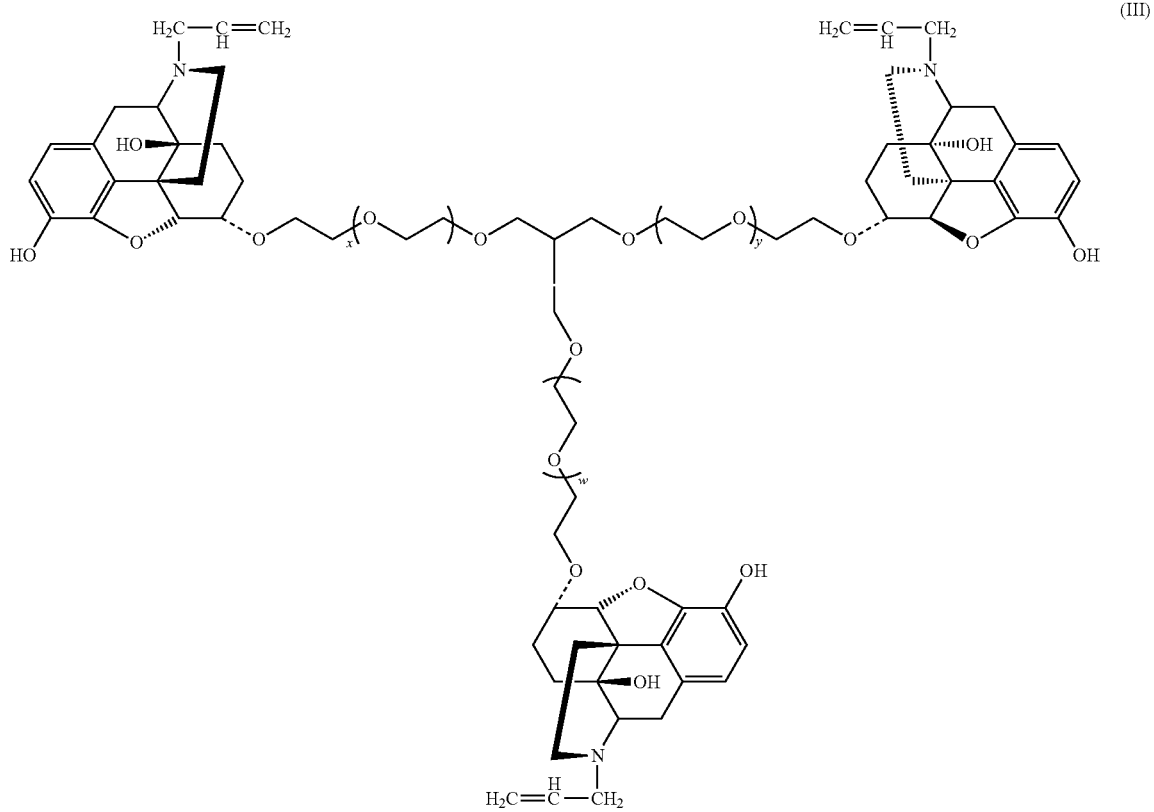

(III)

wherein x, y and w are the same or different, and are each an integer in the range of 0 to 20. Preferably, x, y and w are the same or different, and are each an integer in the range of 0 to 15. More preferably, x, y and w are the same, and are an integer in the range of 0 to 10. Even more preferably, x, y and w may be the same or different, and are each an integer in the range of 0 to 9, 0 to 8, 0 to 7 or 0 to 6.

In some embodiments, the conjugate is in a configuration of (α,α,α), (β,β,β), (α,α,β) or a mixture thereof. A preferred configuration is (α,α,α) or (β,β,β).

A further aspect of the present invention provides a PEG-naloxone conjugate of general formula (IV) or a pharmaceutically acceptable salt thereof:

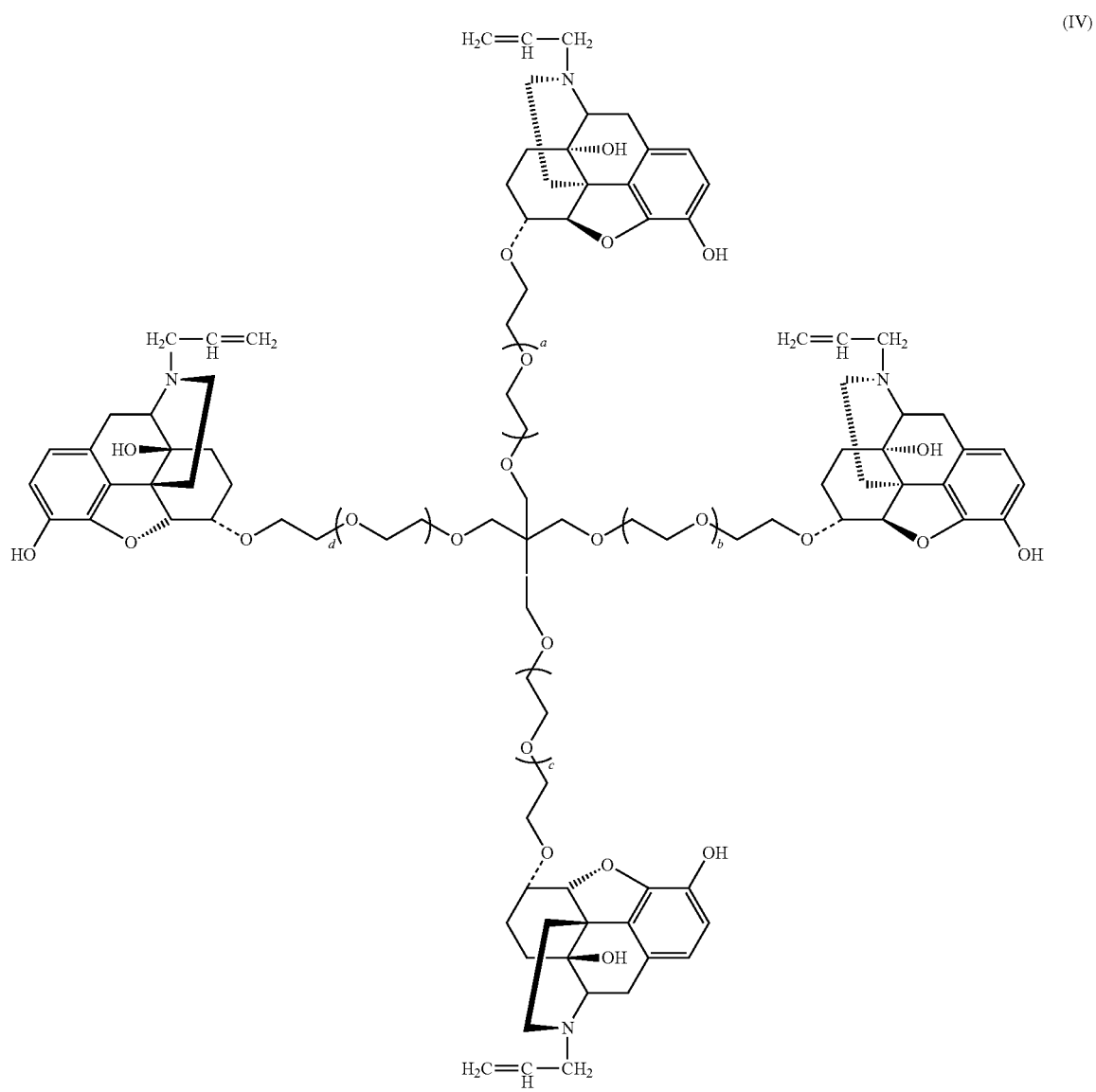

(IV)

wherein a, b, c and d are the same or different, and are each an integer in the range of 0 to 20. Preferably, a, b, c and d are the same or different, and are each an integer in the range of 0 to 15. More preferably, a, b, c and d are the same, and are each an integer in the range of 0 to 10. Even more preferably, a, b, c and d may be the same or different, and are each an integer in the range of 0 to 8, 0 to 7, 0 to 6 or 0 to 5.

In some embodiments, the conjugate is in a configuration of (α,α,α,α), (β,β,β,β), (α,β,β,β), (α,α,β,β), (α,α,α,β) or a mixture thereof. A preferred configuration is (α,α,α,α) or (β,β,β,β).

The above-mentioned pharmaceutically acceptable salt may be hydrochloride, hydrobromide, sulfate, nitrate, phosphate, citrate, tartrate, fumarate, maleate, lactate, benzenesulfonate, pantothenate, ascorbate, or the like, or a combination thereof.

A further aspect of the present invention provides a pharmaceutical composition comprising the PEG-naloxone conjugate or pharmaceutically acceptable salt thereof. The pharmaceutical composition may further comprise a pharmaceutically acceptable carrier or excipient.

In some embodiments, the pharmaceutical composition may form tablets, injections, suppositories, pills, soft or hard gelatin capsules, powders, solutions, suspensions or aerosols.

A further aspect of the present invention provides use of the PEG-naloxone conjugate or pharmaceutically acceptable salt thereof in the preparation of a medicament for the treatment of bowel dysfunction and constipation caused by chronic administration of opioids.

The present invention has the advantage that naloxone can be protected by modification with the hydrophilic polymer PEG to improve drug absorption, change the in vivo distribution of the drug, reduce the penetration through blood-brain barrier, and avoid side effects.

MODE FOR CARRYING OUT THE INVENTION

Low molecular weight PEG is introduced in naloxone molecules by the technique of PEGylation to increase the hydrophilicity and improve the in vivo distribution of the drug, reduce the penetration thereof through blood-brain barrier, and thus reduce the toxicity thereof.

The conjugate of the present invention is prepared by the following process: modifying hydrophilic oligomeric ethylene glycol by introducing a leaving group such as a halogen atom, a mesyl group or a p-toluene sulfonyl group, and then conjugating it with naloxone under alkaline conditions. The introduction of the oligomeric ethylene glycol changes the in vivo distribution of the drug, improves the penetration through blood-brain barrier, and alleviates bowel dysfunction and constipation caused by chronic administration of opioids.

The oligomeric ethylene glycol is characterized by polymeric ethylene glycol units, and in general, by the number of ethylene glycol units, which is in the range of 0 to 20, preferably 0 to 10.

The term polyethylene glycol in the present invention also contemplates derivatives and analogues of PEG, and can also be replaced by a hydrophilic polymer selected from the group consisting of polyethylene glycol, poly(glutamic acid), poly (aspartic acid), polypropylene glycol, polyvinyl alcohol, polyacryloyl morpholine, polyoxazoline and copolymers thereof.

The conjugate of the present invention may be administrated in the form of a pure compound or a suitable pharmaceutical composition, and any acceptable modes of administration or reagents for similar use can be employed. Therefore, the mode of administration can be oral, intranasal, parenteral, topical, transdermal or rectal, and the dosage form is solid, semi-solid or liquid, such as tablets, suppositories, pills, soft and hard gelatin capsules, powders, solutions, suspensions, or aerosols. Preferably, a dosage unit form suitable for simple administration with precise dosage is employed. The composition may contain the conjugate(s) of the present invention as active ingredients, and conventional pharmaceutical carriers or excipients, as well as other agents, carriers, adjuvants, and the like.

Typically, depending on the desired mode of administration, the pharmaceutical composition contains about 1 wt. % to 99 wt. % of the conjugate(s) of the present invention and 99 wt. % to 1 wt. % of suitable pharmaceutical excipients. Preferably, the composition contains about 5 wt. % to 75 wt. % of the conjugate(s) of the present invention, and a balance of suitable pharmaceutical excipients.

The pharmaceutical composition can be administered in the form of a liquid. For example, the conjugate(s) of the present invention (about 0.5% to 20%) and the optional pharmaceutical adjuvants can be dissolved or dispersed in the carriers such as water, saline, aqueous dextrose, glycerol and ethanol to form a solution or suspension.

If desired, the pharmaceutical composition of the present invention may contain small amounts of adjuvants such as wetting agents or emulsifying agents, pH buffering agents and antioxidants, e.g. citric acid, sorbitan monolaurate, triethanolamine oleate, butylated hydroxytoluene, or the like.

The present invention will be illustrated with the following examples, which, however, do not limit the invention.

EXAMPLES

In the examples, Naloxone hydrochloride was provided by Beijing Yidong Bojie Technology Co., Ltd., methoxyethoxymethyl chloride (MEMCl) was purchased from alfa Aesar, p-tosyl chloride was purchased from Shandong Yilong Industrial Co., Ltd., sodium hydride was purchased from TCI (Shanghai) Chemical Industrial Co., Ltd., H(OCH$_2$CH$_2$)$_4$—OH, H(OCH$_2$CH$_2$)$_6$—OH and H(OCH$_2$CH$_2$)$_{12}$—OH were purchased from Jainxin Bomei Biotechnology Co., Ltd. Other reagents used in the examples of the invention were all chemically pure reagents that were commercially available.

Example 1

Synthesis of Double-End Substituted Hexaethylene Glycol-Naloxone (α,α)-NAL26 and (β,β)-NAL26 (Compounds E2 and E1, wherein f=6)

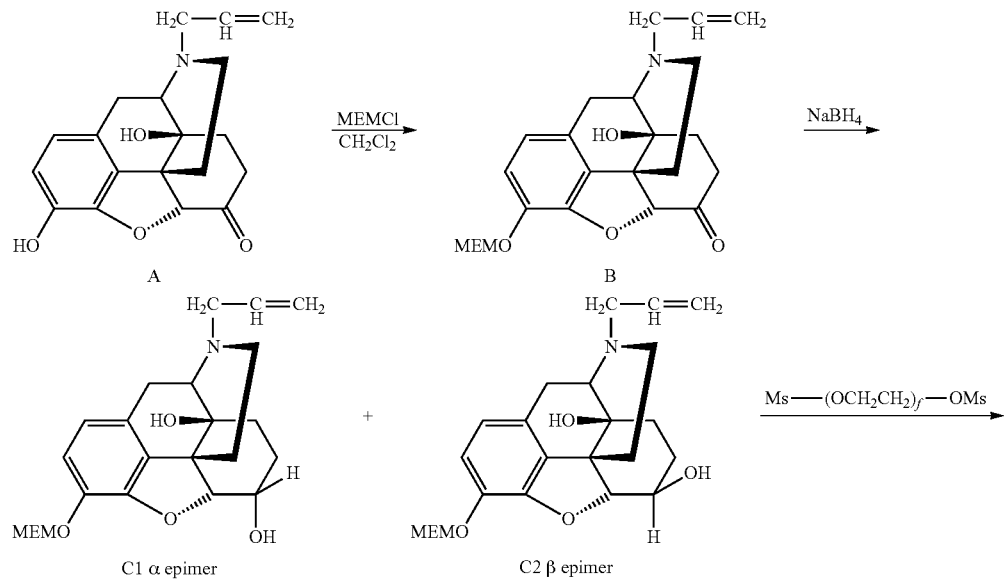

-continued

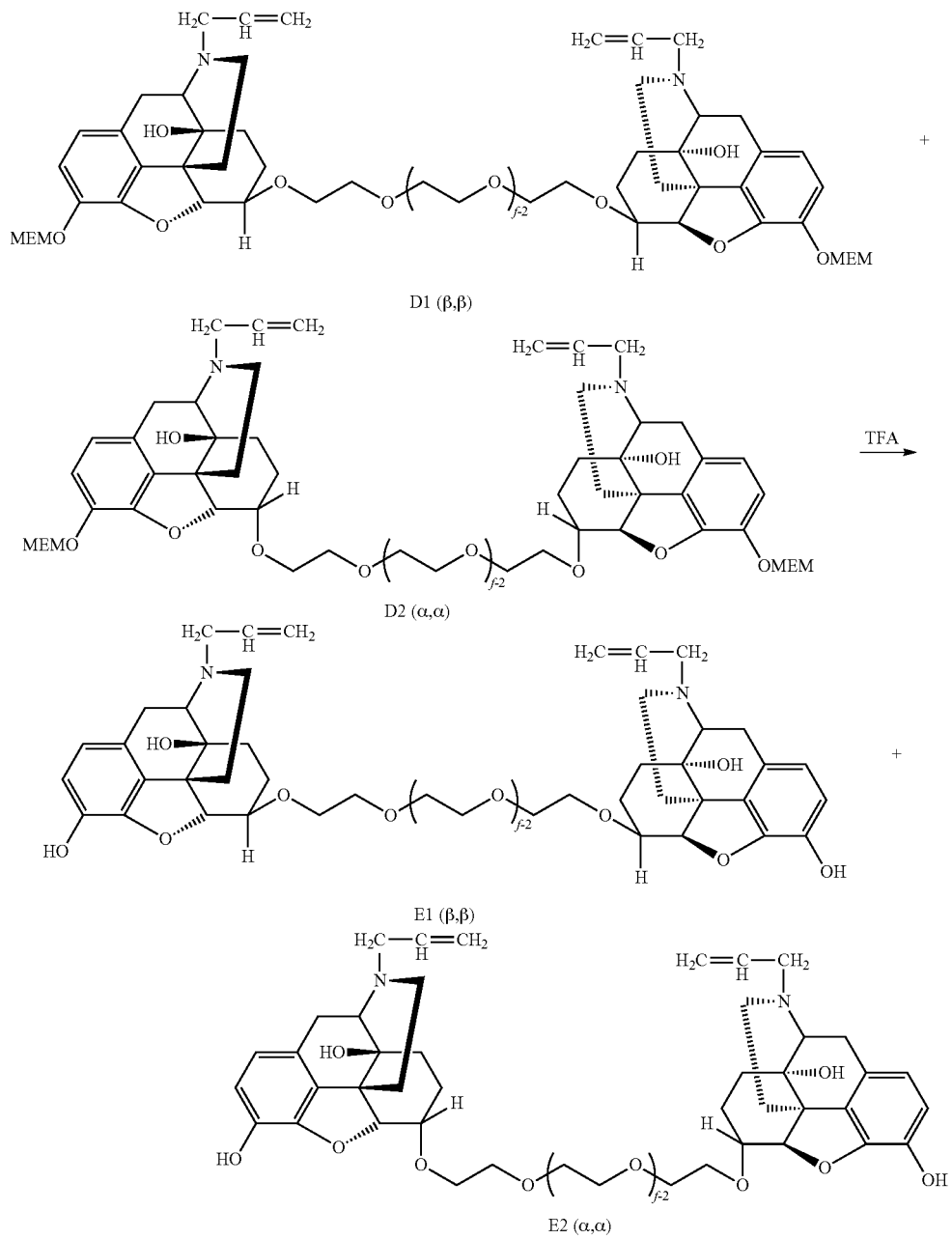

Synthesis of Compound B:

6 g Naloxone hydrochloride A was added into a round bottom flask and dissolved in 30 ml dichloromethane. 11.7 g di-isopropylethylamine (DIPEA) was added after complete dissolution of Naloxone hydrochloride A. The mixture was stirred under nitrogen for 15 min before 7.6 g MEMCl was added slowly and dropwise into the solution. Then reaction was allowed at room temperature for 24 h. After complete reaction monitored by TLC, stirring was stopped, and water was added three times (30 ml×3) for extraction. The organic phase was washed once with a saturated sodium chloride solution before it was dried over anhydrous sodium sulfate. Concentration and purification by column chromatography offered 5.37 g Compound B with a yield of 87%.

Synthesis of Compound C1 (α Configuration) and Compound C2 (β Configuration):

5.37 g Compound B, 180 ml ethanol, and 90 ml 0.2 N sodium hydroxide solution were added into a round bottom flask, and were stirred for 15 min. 2.3 g Sodium borohydride was added in batches, and the mixture was then stirred at room temperature overnight. After complete reaction monitored by TLC, stirring was stopped. The reaction mixture was concentrated and extracted three times with dichloromethane (100 ml×3). The organic phase was washed once with a saturated sodium chloride solution, and dried over anhydrous sodium sulfate for two hours. 4.7 g crude product was obtained upon concentration. Purification by column chromatography offered 1.66 g Compound C1 (α configuration)

and 1.80 g Compound C2 (β configuration) with yields of 31% and 33%, respectively.

Synthesis of Compound D1 (β,β) and Compound D2 (α,α):

22.9 g p-toluenesulfonyl chloride and 80 ml pyridine were added into a 500 ml three-necked flask, and the mixture was cooled to 0° C. 14.1 g H—(OCH$_2$CH$_2$)$_6$—OH was mixed with 40 ml pyridine, and the mixture was added dropwise into the three-necked flask while controlling the temperature in the range of 0-10° C. The reaction mixture was stirred and allowed to react at this temperature for two hours. Complete reaction was monitored by TLC. 300 ml cold water and 120 ml concentrated hydrochloric acid were added into the reaction solution. The mixture was slowly stirred for half an hour, then transferred into a 1000 ml separatory funnel, and extracted twice with ethyl acetate (300 ml+200 ml). The organic layers were combined, washed with water to a neutral pH value, and dried over anhydrous sodium sulfate for two hours. The solvent was evaporated with a rotary evaporator. 28.7 g viscous liquid of Ms-(OCH$_2$CH$_2$)$_6$—OMs was obtained and directly applied in the next reaction.

801 mg Compound C1 purified by column chromatography was added into a round bottom flask, and 3 ml dimethyl formamide (DMF) was added. After Compound C1 was completely dissolved in DMF, 421 mg Ms-(OCH$_2$CH$_2$)$_6$-OMs was added, and then 384 mg sodium hydride was added in portions. The mixture was allowed to react at 30° C. overnight. After complete reaction monitored by TLC, stirring was stopped, and 100 ml water was added before the mixture was extracted three times with dichloromethane (100 ml×3). The organic phase was washed once with a saturated sodium chloride solution, and dried over anhydrous sodium sulfate for two hours. A crude product was obtained upon concentration, and purification by column chromatography offered 335 mg Compound D1 (β,β) with a yield of 23.2%.

Compound D2 (α,α) was synthesized in a same way as that for Compound D1.

Synthesis of Compound E1 (β,β) and Compound E2 (α,α):

150 mg Compound D1 (β,β) was dissolved in 5 ml anhydrous methanol, and hydrogen chloride gas was bubbled into the solution. After complete reaction monitored by TLC, stirring was stopped. The mixture was concentrated and adjusted to pH 9 through slow addition of a potassium carbonate aqueous solution. The mixture was extracted three times with ethyl acetate (100 ml×3). The organic phase was washed once with a saturated sodium chloride solution, and dried over anhydrous sodium sulfate for two hours. A crude product was obtained upon concentration, and purification by column chromatography offered 98 mg Compound E1 (β,β) with a yield of 91%. m/z [MH]$^+$ 907.2. $^1$H-NMR (DMSO-d$_6$): 1.25-1.35 (m, 4H), 1.45 (d, 2H), 1.55-1.60 (m, 2H), 1.75-1.88 (m, 4H), 2.1-2.2 (m, 4H), 2.49-2.59 (m, 4H), 2.88 (d, 2H), 3.00-3.10 (m, 6H), 3.22 (m, 2H), 3.62-3.77 (m, 24H), 4.52 (d, 2H), 5.12-5.20 (m, 4H), 5.77 (m, 2H), 6.53 (d, J=8.16 Hz, 2H), 6.70 (d, J=8.1 Hz, 2H).

Compound E2 (α,α) was synthesized in a same way as that for Compound E1 (β,β). m/z [MH]$^+$ 907.2. $^1$H-NMR (CDCl$_3$): 1.15-1.25 (m, 4H), 1.45-1.59 (m, 8H), 2.1-2.26 (m, 4H), 2.52-2.61 (m, 4H), 2.88 (d, 2H), 3.00-3.10 (m, 6H), 3.55-3.77 (m, 24H), 3.86-3.88 (m, 2H), 4.71 (d, 2H), 5.14-5.22 (m, 4H), 5.76-5.84 (m, 2H), 6.49 (d, J=8.16 Hz, 2H), 6.70 (d, J=8.1 Hz, 2H).

Example 2

Synthesis of Double-End Substituted Tetraethylene Glycol-Naloxone (α,α)-NAL24 (Compound E2, wherein f=4)

Except that tetraethylene glycol was used instead of hexaethylene glycol, the procedure of Example 1 was repeated to obtain the double-end substituted tetraethylene glycol-naloxone (α,α)-NAL24. m/z [MH]$^+$ 817. $^1$H-NMR (CDCl$_3$): 1.14-1.24 (m, 4H), 1.46-1.58 (m, 8H), 2.1-2.23 (m, 4H), 2.52-2.62 (m, 4H), 2.89 (d, 2H), 3.00-3.11 (m, 6H), 3.55-3.78 (m, 16H), 3.86-3.89 (m, 2H), 4.72 (d, 2H), 5.15-5.21 (m, 4H), 5.77-5.85 (m, 2H), 6.50 (d, J=8.16 Hz, 2H), 6.71 (d, J=8.1 Hz, 2H).

Example 3

Synthesis of Double-End Substituted Dodecaethylene Glycol-Naloxone (α,α)-NAL212 (Compound E2, wherein f=12)

Except that H(OCH$_2$CH$_2$)$_{12}$—OH was used instead of hexaethylene glycol, the procedure of Example 1 was repeated to obtain the double-end substituted dodecaethylene glycol-naloxone (α,α)-NAL212. m/z [MH]$^+$ 1169. $^1$H-NMR (CDCl$_3$): 1.12-1.24 (m, 4H), 1.45-1.589 (m, 8H), 2.11-2.24 (m, 4H), 2.50-2.61 (m, 4H), 2.89 (d, 2H), 3.02-3.11 (m, 6H), 3.50-3.78 (m, 48H), 3.86-3.90 (m, 2H), 4.71 (d, 2H), 5.14-5.20 (m, 4H), 5.75-5.85 (m, 2H), 6.51 (d, J=8.17 Hz, 2H), 6.70 (d, J=8.1 Hz, 2H).

Example 4

Synthesis of a Three-Branched Ethylene Glycol-Naloxone Conjugate (NAL31) (Compound K)

The three-branched ethylene glycol (H) was synthesized in reference to US2006/0047167.

Synthesis of Compound I:

17.2 g p-toluenesulfonyl chloride and 40 ml pyridine were added into a 250 ml three-necked flask, and the mixture was cooled to 0° C. 7.14 g Compound H was mixed with 20 ml pyridine, and the mixture was added dropwise into the three-necked flask while controlling the temperature in the range of 0-10° C. The reaction mixture was stirred and allowed to react at this temperature for two hours. Complete reaction was monitored by TLC. 100 ml cold water and 60 ml concentrated hydrochloric acid were added into the reaction solution. The mixture was slowly stirred for half an hour, then transferred into a 1000 ml separatory funnel, and extracted twice with ethyl acetate (300 ml+200 ml). The organic layers were combined, washed with water to a neutral pH value, and dried over anhydrous sodium sulfate for two hours. The solvent was evaporated with a rotary evaporator. 13.7 g viscous liquid was obtained and directly applied in the next reaction.

Synthesis of Compound J:

626 mg Compound C1 purified by column chromatography was added into a round bottom flask, and 3 ml DMF was added. After Compound C1 was completely dissolved in DMF, 236 mg Compound I was added, and 284 mg sodium hydride was added in portions. The mixture was allowed to react at 30° C. overnight. After complete reaction monitored by TLC, stirring was stopped, and 100 ml water was added before the mixture was extracted three times with dichloromethane (100 ml×3). The organic phase was washed once with a saturated sodium chloride solution, and dried over anhydrous sodium sulfate for two hours. A crude product was obtained upon concentration, and purification by column chromatography offered 243 mg Compound J with a yield of 16.9%.

Synthesis of Compound K:

243 mg Compound J was dissolved in 5 ml anhydrous methanol, and hydrogen chloride gas was bubbled into the solution. After complete reaction monitored by TLC, stirring was stopped. The mixture was concentrated and adjusted to pH 9 through slow addition of a potassium carbonate aqueous solution. The mixture was extracted three times with dichloromethane (100 ml×3). The organic phase was washed once with a saturated sodium chloride solution, and dried over anhydrous sodium sulfate for two hours. A crude product was obtained upon concentration, and purification by column chromatography offered 168 mg Compound K with a yield of 84.8%. m/z [MH]$^+$ 1171.6. $^1$H-NMR (DMSO-d$_6$): 1.24-1.35 (m, 6H), 1.46 (d, 3H), 1.57-1.62 (m, 3H), 1.77-1.88 (m, 6H), 2.0-2.2 (m, 6H), 2.50-2.59 (m, 6H), 2.66 (m, 1H), 2.86 (d, 3H), 3.00-3.09 (m, 9H), 3.23 (m, 3H), 3.60-3.77 (m, 18H), 4.51 (d, 3H), 5.12-5.18 (m, 6H), 5.78 (m, 3H), 6.53 (d, J=8.16 Hz, 3H), 6.70 (d, J=8.1 Hz, 3H).

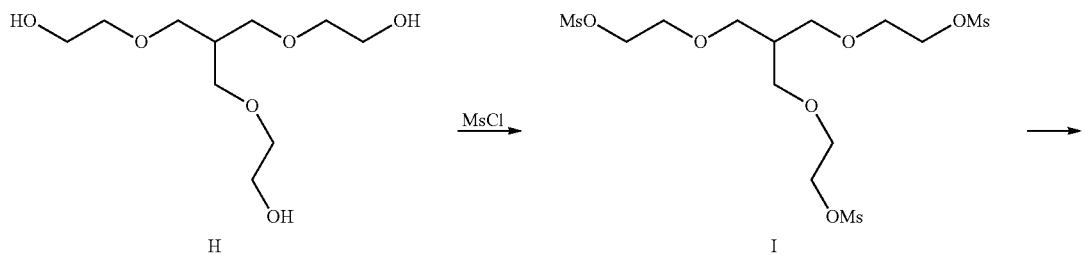

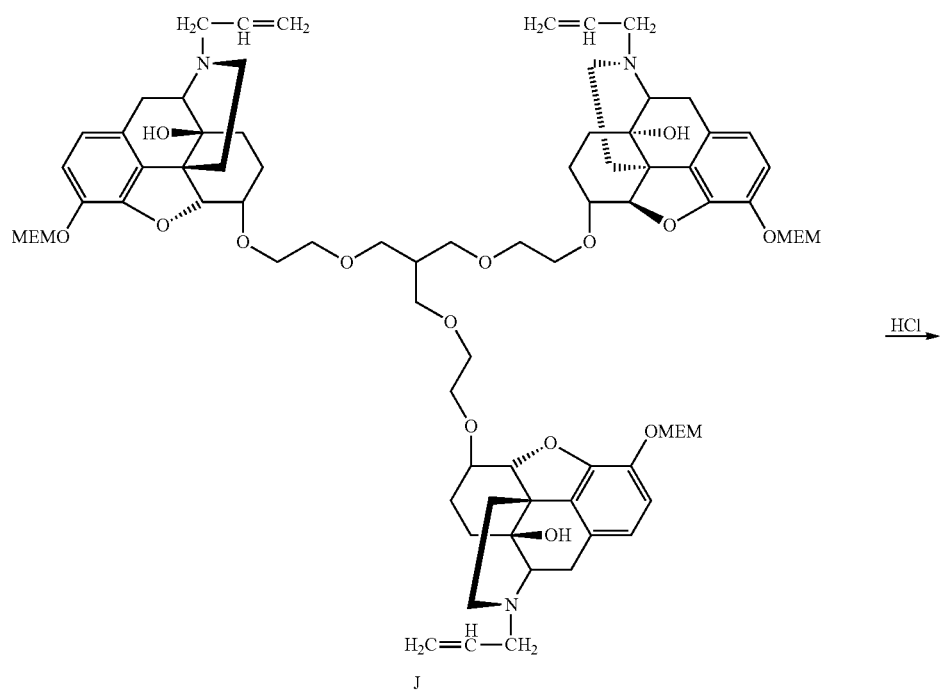

-continued
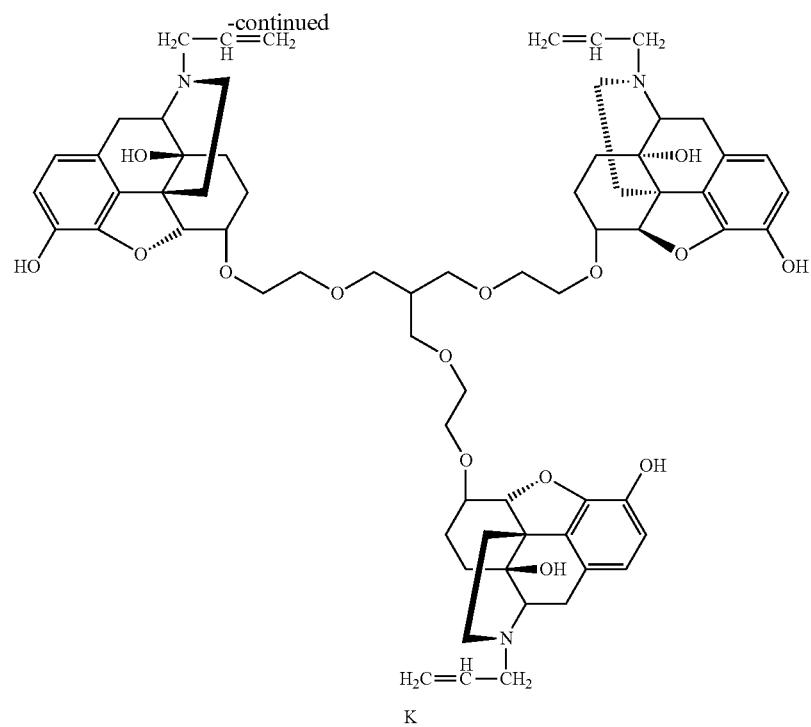
K
Example 5
Synthesis of a Three-Branched Ethylene Glycol-Naloxone Conjugate (NAL37) (Compound N)
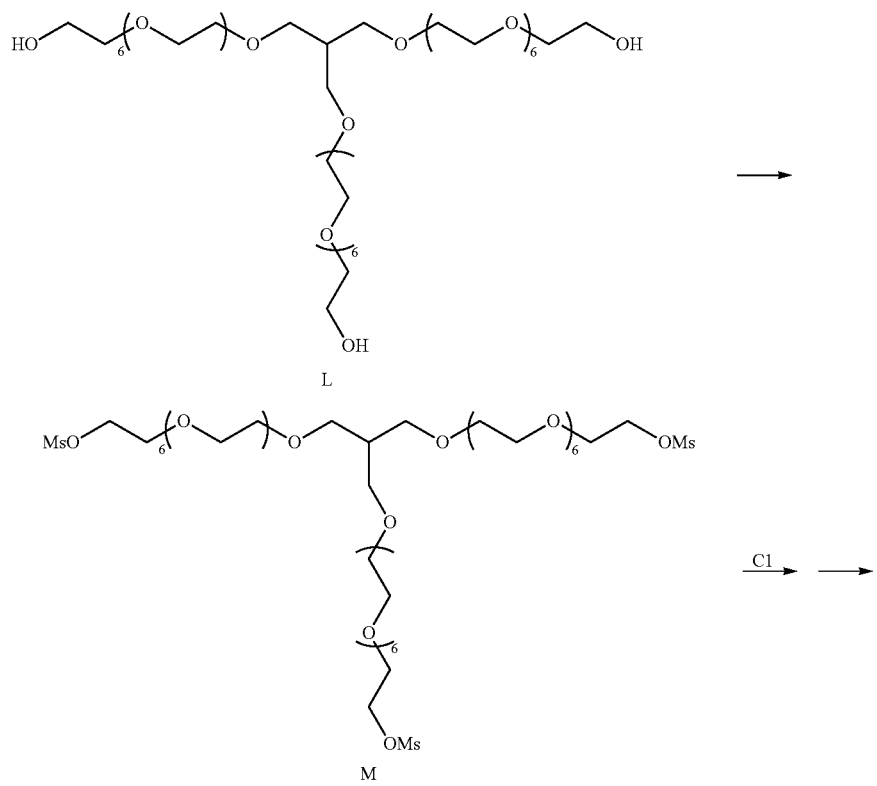

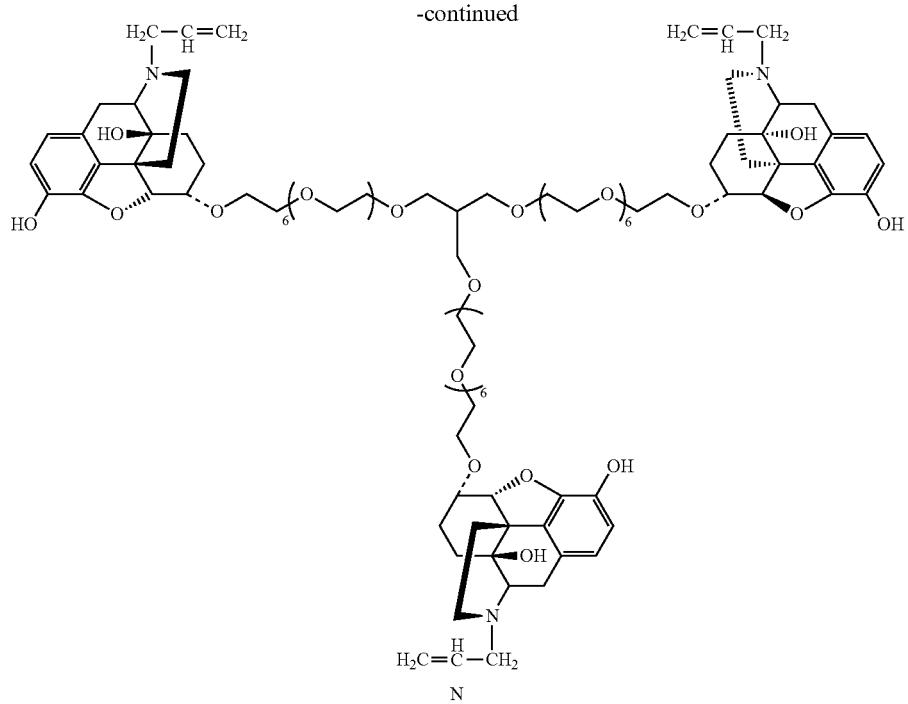

Compound L was synthesized in reference to the literature *J. Org. Chem.* 2006, 71, 9884-9886.

The synthesis of Compound M was similar to that of Compound I in Example 4, with Compound H being replaced with Compound L.

Synthesis of Compound N (NAL37):

Except that Compound L was used instead of Compound H, the procedure of Example 4 was repeated to obtain the three-branched ethylene glycol-naloxone ($\alpha,\alpha$)-NAL37. m/z $[MH]^+$ 1963.6. $^1$H-NMR (DMSO-$d_6$): 1.22-1.35 (m, 6H), 1.47 (d, 3H), 1.57-1.64 (m, 3H), 1.74-1.88 (m, 6H), 2.0-2.22 (m, 6H), 2.50-2.57 (m, 6H), 2.68 (m, 1H), 2.88 (d, 3H), 3.01-3.08 (m, 9H), 3.24 (m, 3H), 3.55-3.78 (m, 90H), 4.52 (d, 3H), 5.11-5.18 (m, 6H), 5.77 (m, 3H), 6.54 (d, J=8.16 Hz, 3H), 6.71 (d, J=8.1 Hz, 3H).

Example 6

Synthesis of a Four-Branched Ethylene Glycol-Naloxone Conjugate (NAL41) (Compound Q)

The four-branched ethylene glycol ($M_1$) was synthesized in reference to Bulletin of Academy of Sciences of the USSR, Division of Chemical Science (English Translation); vol 38; nb 10; (1989); p 2207.

Synthesis of Compound $N_1$:

19.06 g p-toluenesulfonyl chloride and 40 ml pyridine were added into a 250 ml three-necked flask, and the mixture was cooled to 0° C. 7.8 g Compound $M_1$ was mixed with 20 ml pyridine, and the mixture was added dropwise into the three-necked flask while controlling the temperature in the range of 0-10° C. The reaction mixture was stirred and allowed to react at this temperature for two hours. Complete reaction was monitored by TLC. 100 ml cold water and 60 ml concentrated hydrochloric acid were added into the reaction solution. The mixture was slowly stirred for half an hour, then transferred into a 1000 ml separatory funnel, and extracted twice with ethyl acetate (300 ml+200 ml). The organic layers were combined, washed with water to a neutral pH value, and dried over anhydrous sodium sulfate for two hours. The solvent was evaporated with a rotary evaporator. 14.7 g viscous liquid was obtained and directly applied in the next reaction.

Synthesis of Compound P:

834 mg Compound C1 purified by column chromatography was added into a round bottom flask, and 3 ml DMF was added. After Compound C1 was completely dissolved in DMF, 312 mg Compound $N_1$ was added, and 389 mg sodium hydride was added in portions. The mixture was allowed to react at 30° C. overnight. After complete reaction monitored by TLC, stirring was stopped, and 100 ml water was added before the mixture was extracted three times with dichloromethane (100 ml×3). The organic phase was washed once with a saturated sodium chloride solution, and dried over anhydrous sodium sulfate. A crude product was obtained upon concentration, and purification by column chromatography offered 136 mg Compound P with a yield of 16.3%.

Synthesis of Compound Q:

136 mg Compound P was dissolved in 5 ml anhydrous methanol, and hydrogen chloride gas was bubbled into the solution. After complete reaction monitored by TLC, stirring was stopped. The mixture was concentrated and adjusted to pH 9 through slow addition of a potassium carbonate aqueous solution. The mixture was extracted three times with ethyl acetate (100 ml×3). The organic phase was washed once with a saturated sodium chloride solution, and dried over anhydrous sodium sulfate. A crude product was obtained upon concentration, and purification by column chromatography offered 85 mg Compound Q with a yield of 76.6%. m/z $[MH]^+$ 1556.7. $^1$H-NMR (DMSO-$d_6$): 1.24-1.33 (m, 8H), 1.47 (d, 4H), 1.55-1.60 (m, 4H), 1.74-1.89 (m, 8H), 2.1-2.22 (m, 8H), 2.47-2.61 (m, 8H), 2.89 (d, 4H), 3.01-3.11 (m, 12H), 3.23 (m, 4H), 3.61-3.79 (m, 24H), 4.54 (d, 4H), 5.11-5.18 (m, 8H), 5.79 (m, 4H), 6.54 (d, J=8.16 Hz, 4H), 6.70 (d, J=8.1 Hz, 4H).

19
20
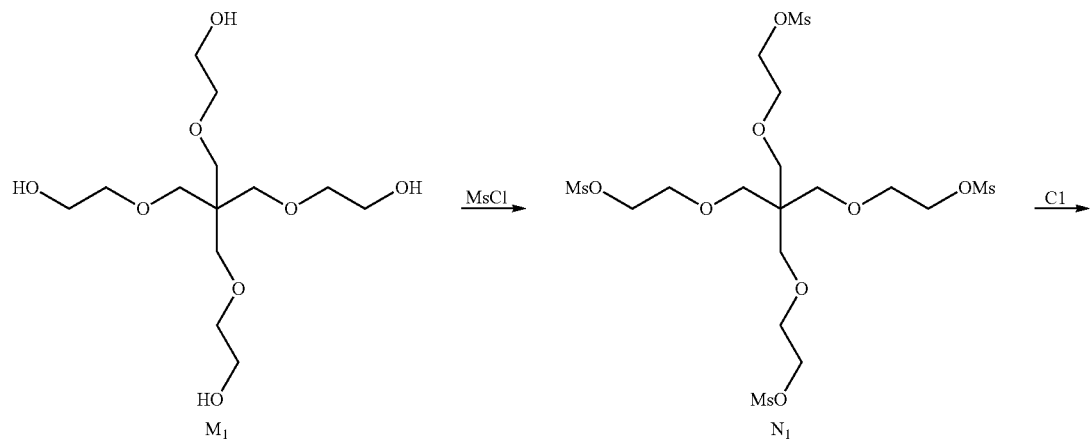
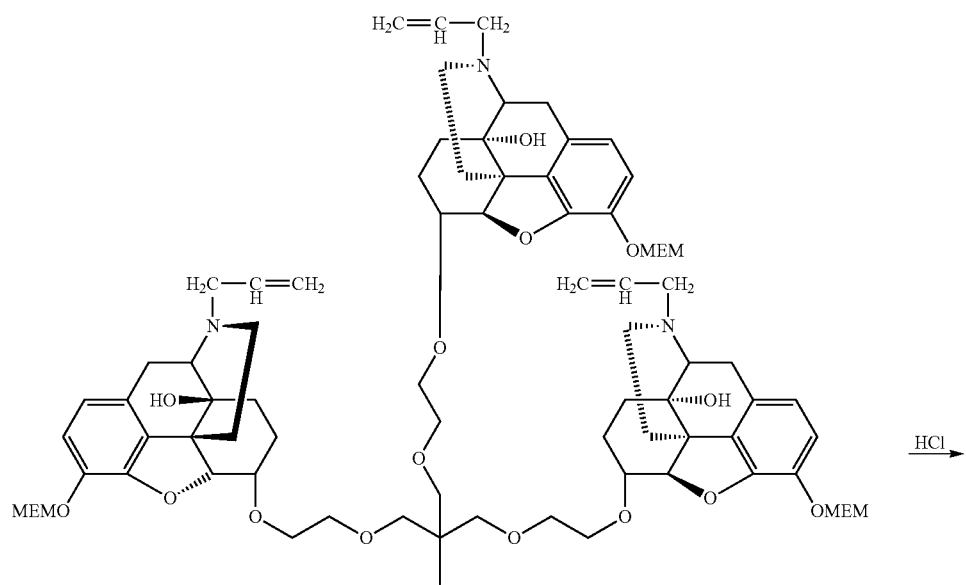
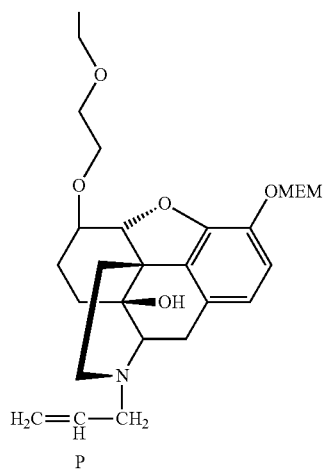

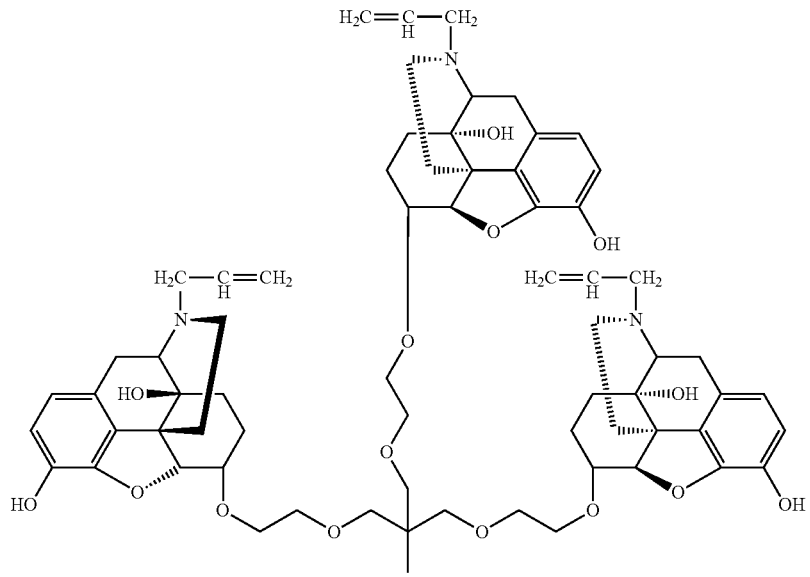

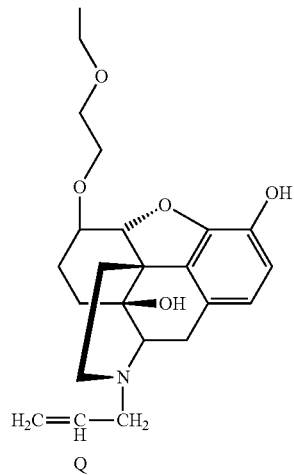

Q

Example 7

Synthesis of a Four-Branched Ethylene Glycol-Naloxone Conjugate (NAL46) (Compound T)

Compound R was synthesized in reference to *J. Org. Chem.* 2006, 71, 9884-9886.

The synthesis of Compound S was similar to that of Compound $N_1$ in Example 6, with Compound $M_1$ being replaced with Compound R.

Synthesis of Compound T (NAL46):

Except that Compound R was used instead of Compound $M_1$, the procedure of Example 6 was repeated to obtain the four-branched ethylene glycol-naloxone (α,α)-NAL46. m/z [MH]$^+$ 2436.9. $^1$H-NMR (DMSO-d$_6$): 1.24-1.35 (m, 8H), 1.43 (d, 4H), 1.55-1.64 (m, 4H), 1.74-1.89 (m, 8H), 2.1-2.20 (m, 8H), 2.47-2.60 (m, 8H), 2.87 (d, 4H), 3.01-3.15 (m, 12H), 3.25 (m, 4H), 3.55-3.79 (m, 104H), 4.58 (d, 4H), 5.11-5.20 (m, 8H), 5.78 (m, 4H), 6.56 (d, J=8.16 Hz, 4H), 6.72 (d, J=8.1 Hz, 4H).

23
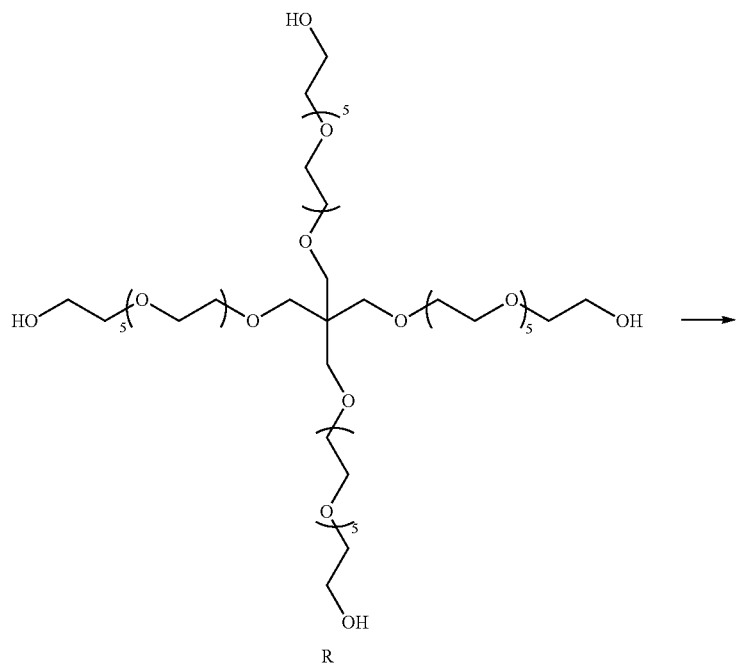
R
24
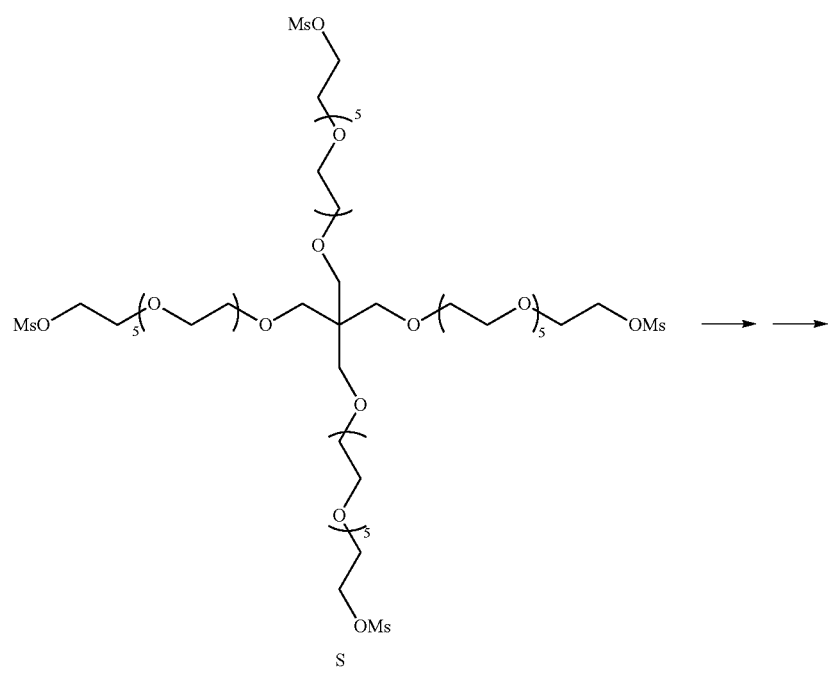
S

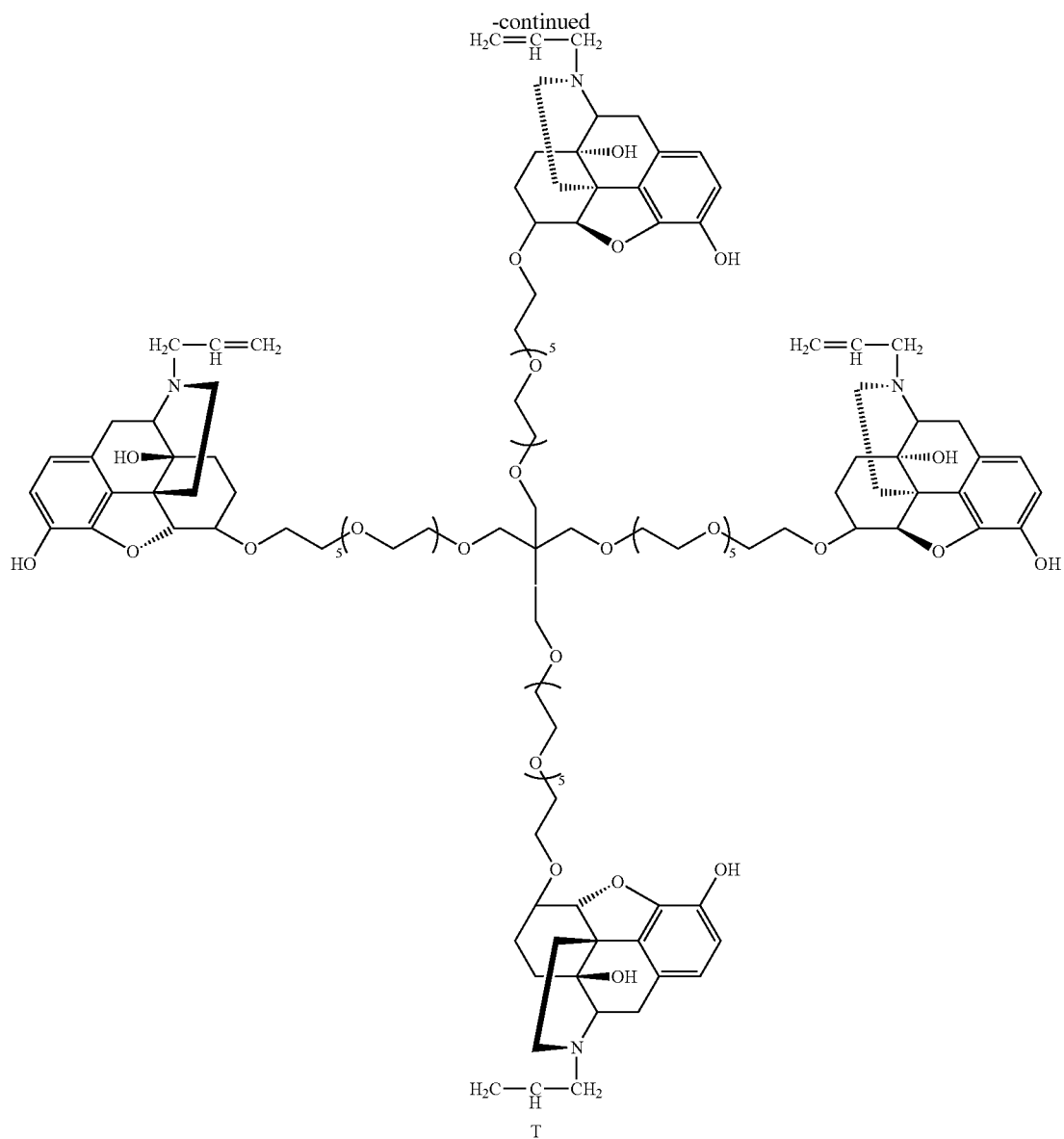

Example 8

Antagonism of PEG-Naloxone Conjugates Against MOR Receptors

Test Substances:

A total of six samples, namely the double-end substituted hexaethylene glycol-naloxone (α,α)-NAL26 and (β,β)-NAL26, the double-end substituted tetraethylene glycol-naloxone (α,α)-NAL24, and the single-end substituted pantaethylene glycol-naloxone α-m-NAL5 and β-m-NAL5 (provided by Beijing Jiankai Science and Technology Co., Ltd.) and naloxone, were used as test substances.

Positive Control:

Beta-FNA, provided by the National Center for Drug Screening, was diluted to desired concentrations with a calcium buffer solution immediately before use.

Naloxone, provided by Beijing Yidong Bojie Technology Co., Ltd., was diluted to desired concentrations with a calcium buffer solution immediately before use.

Test Mechanism:

A cell line co-transfected with MOR and Gα16 is established, such that activation of receptors can activate Ga16 protein, which in turn activates phospholipase C (PLC) to generate IP3 and DAG. IP3 can bind to IP3 receptors on endoplasmic reticulum and mitochondria in the cells, thereby triggering the release of intracellular calcium. Therefore, detection of intracellular calcium levels can be employed as a measure for detecting the activation state of MOR. Fluo-4/AM is a calcium fluorescent probe indicator for measuring calcium ions. It is a non-polar liposoluble compound, which, upon entering a cell and by the action of lipolytic enzymes, releases Fluo-4 while the AM moiety is dissociated. As a polar molecule, Fluo-4 cannot easily pass through the lipid bilayer membrane, thus it is retained in the cells for a long duration. Eventually, the level of activation of Gα proteins is reflected by measuring the intensity of fluorescence that is excited. If the compounds to be screened are capable of antagonizing MOR receptors, calcium flux would be greatly reduced.

Test Procedures:
1. inoculating CHO cells stably expressing MOR/Gα16 in a 96-well plate and incubating the same overnight;
2. removing the medium from the wells inoculated with cells, adding freshly prepared dye (40 μl/well), and incubating for 40 minutes in a thermostatic incubator of 37° C.;
3. diluting the test substances with a calcium buffer and homogenizing;
4. thoroughly removing and discarding the dye, washing the wells once with a freshly prepared calcium buffer before replacing the buffer with 50 μl calcium buffer having the test substances dissolved therein;
5. detecting with a FlexStation II instrument, wherein 25 μl calcium buffer having known MOR receptor agonists dissolved therein were automatically added at 15 seconds by the instrument, and eventually reading the fluorescent values at 525 nm; and
6. data processing % Response=$(D-B)/(S-B) \times 100\%$;

wherein D is the peak value of calcium-flux caused by the test substances, B is the peak value of calcium-flux caused by a blank calcium buffer, and S is the peak value of calcium-flux caused by the known agonist DAMGO.

Test Results:
All the six test substances had antagonistic effects on MOR receptors:

| Compounds | Mw | $IC_{50}$ (M) | 95% CI (M) |
|---|---|---|---|
| Beta-FNA | | 2.619e-009 | 1.370e-009 to 5.008e-009 |
| NAL | 365.85 | 1.524e-008 | 8.488e-009 to 2.737e-008 |
| (α,α)-NAL26 | 905.08 | 9.555e-009 | 4.225e-009 to 2.161e-008 |
| (β,β)-NAL26 | 905.08 | 2.344e-008 | 1.289e-008 to 4.186e-008 |
| (α,α)-NAL24 | 816.98 | 7.156e-009 | 3.799e-009 to 1.348e-008 |
| A-m-NAL5 | 579.72 | 3.369e-009 | 8.702e-009 to 1.305e-007 |
| β-m-NAL5 | 579.72 | 7.814e-008 | 3.140e-008 to 1.945e-007 |

We claim:

1. A PEG-naloxone conjugate of general formula (II) or a pharmaceutically acceptable salt thereof:

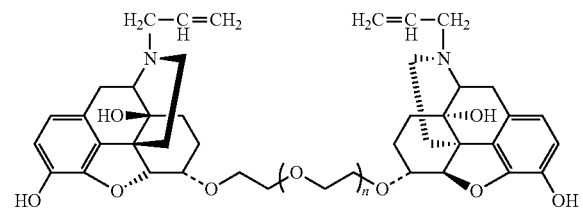

(II)

wherein n is an integer in the range of 1 to 20.

2. The PEG-naloxone conjugate or the pharmaceutically acceptable salt thereof according to claim 1, wherein n is an integer in the range of 1 to 15.

3. The PEG-naloxone conjugate or the pharmaceutically acceptable salt thereof according to claim 1, wherein n is an integer in the range of 2 to 15.

4. The PEG-naloxone conjugate or the pharmaceutically acceptable salt thereof according to claim 1, wherein the conjugate is in a configuration of (α,α), (β,β), (α,β) or a mixture thereof.

5. The PEG-naloxone conjugate or the pharmaceutically acceptable salt thereof according to claim 4, wherein the conjugate is in a configuration of (α,α).

6. The PEG-naloxone conjugate or the pharmaceutically acceptable salt thereof according to claim 4, wherein the conjugate is in a configuration of (β,β).

7. The PEG-naloxone conjugate or the pharmaceutically acceptable salt thereof according to claim 1, wherein the conjugate is selected from the group consisting of conjugates of the following structure:

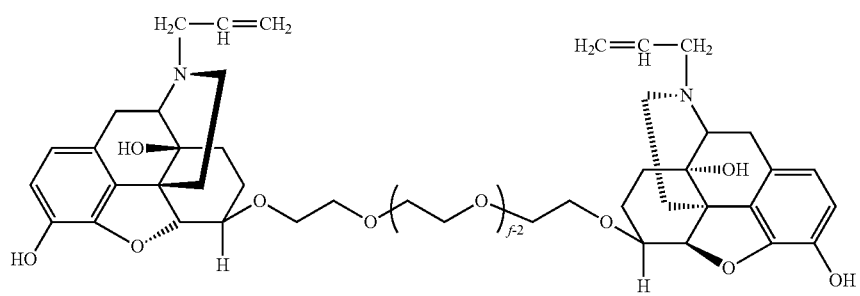

E1 (β, β)

or

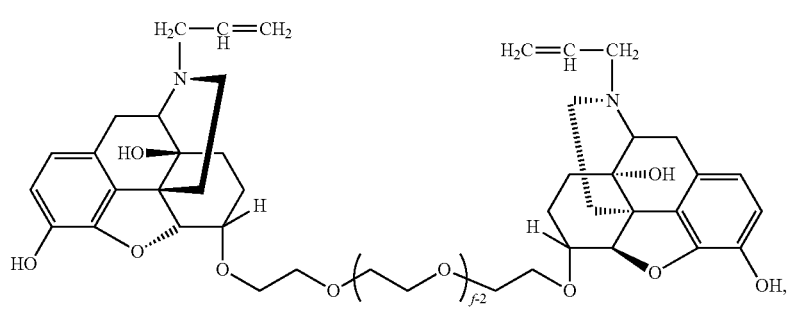

E2 (α, α)

wherein f is 4, 6 or 12.

8. A PEG-naloxone conjugate of general formula (III) or a pharmaceutically acceptable salt thereof:

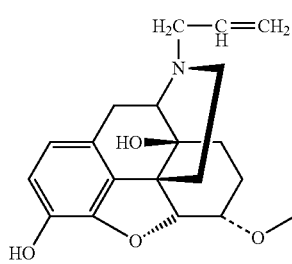
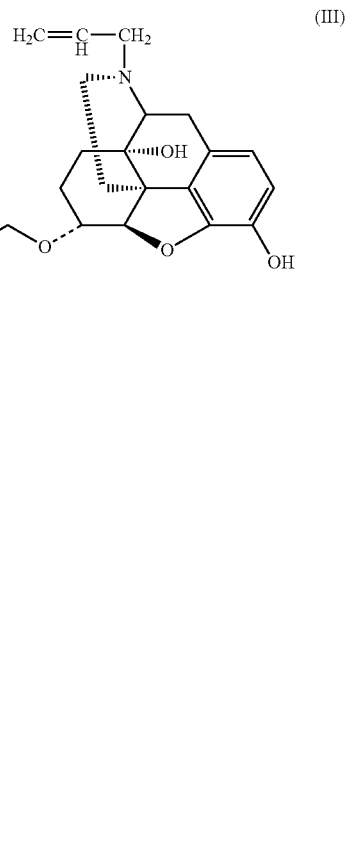

(III)
wherein x, y, w are the same or different, and are each an integer in the range of 0 to 20.

9. The PEG-naloxone conjugate or the pharmaceutically acceptable salt thereof according to claim 8, wherein x, y and w are the same or different, and are each an integer in the range of 0 to 15.

10. The PEG-naloxone conjugate or the pharmaceutically acceptable salt thereof according to claim 8, wherein x, y and w are the same, and are an integer in the range of 0 to 10.

11. The PEG-naloxone conjugate or the pharmaceutically acceptable salt thereof according to claim 8, wherein the conjugate is in a configuration of (α,α,α), (β,β,β), (α,β,β), (α,α,β) or a mixture thereof.

12. The PEG-naloxone conjugate or the pharmaceutically acceptable salt thereof according to claim 11, wherein the conjugate is in a configuration of (α,α,α).

13. The PEG-naloxone conjugate or the pharmaceutically acceptable salt thereof according to claim 11, wherein the conjugate is in a configuration of (β,β,β).

14. The PEG-naloxone conjugate or the pharmaceutically acceptable salt thereof according to claim 8, wherein the conjugate is selected from the group consisting of conjugates of the following structure:

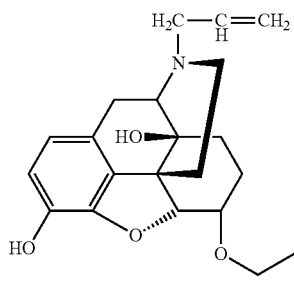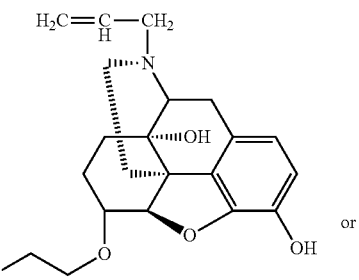 or

-continued
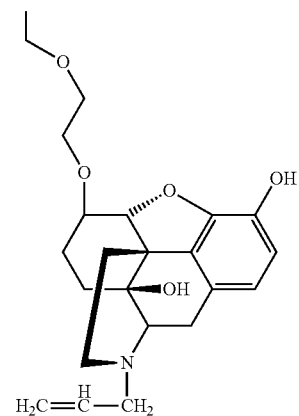
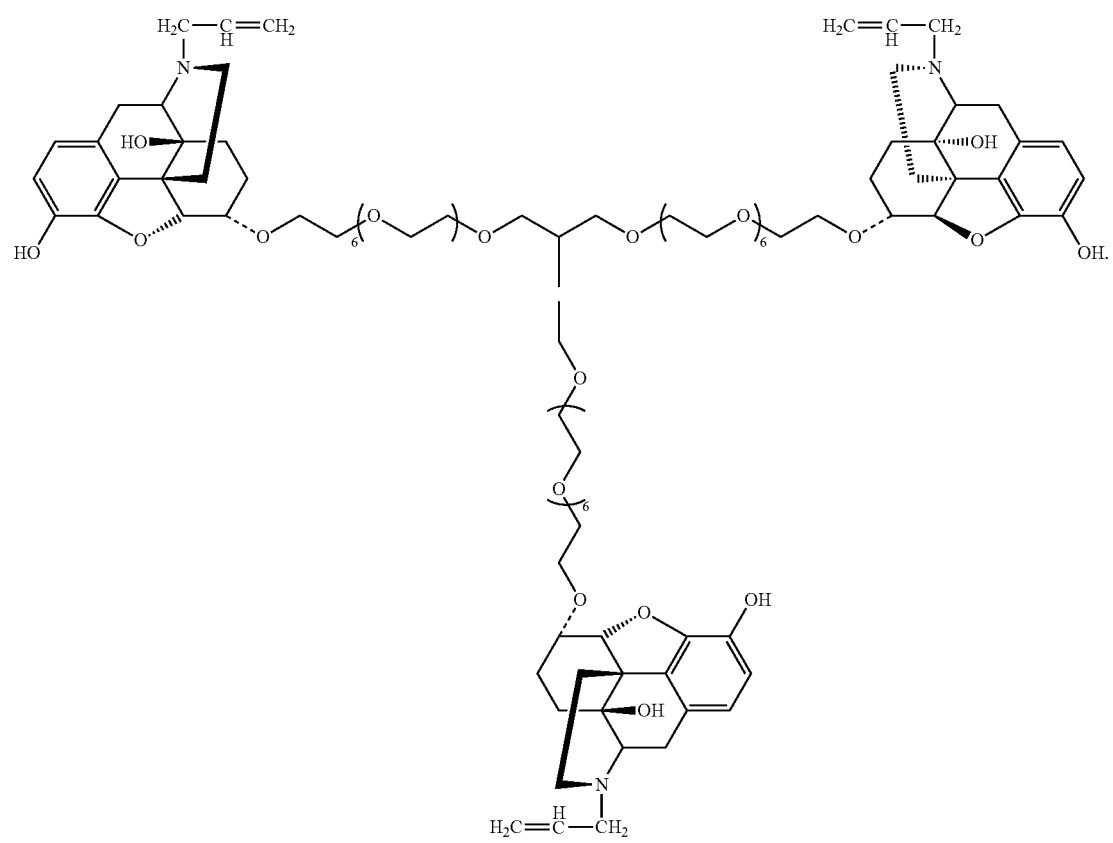

15. A PEG-naloxone conjugate of general formula (IV) or a pharmaceutically acceptable salt thereof:

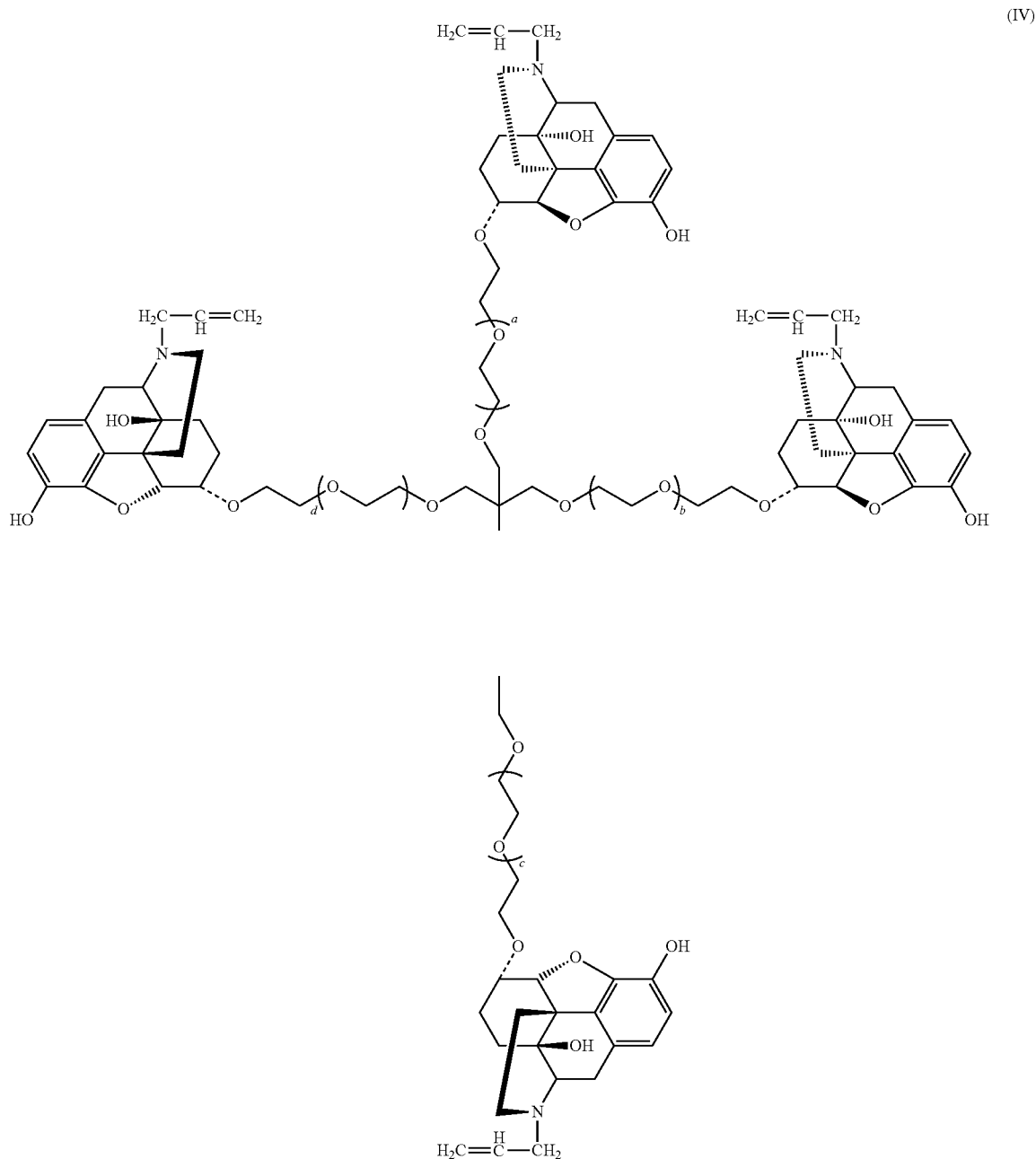

wherein a, b, c and d are the same or different, and are each an integer in the range of 0 to 20.

16. The PEG-naloxone conjugate or the pharmaceutically acceptable salt thereof according to claim 14, wherein a, b, c and d are the same or different, and are each an integer in the range of 0 to 15.

17. The PEG-naloxone conjugate or the pharmaceutically acceptable salt thereof according to claim 14, wherein a, b, c and d are the same, and are an integer in the range of 0 to 10.

18. The PEG-naloxone conjugate or the pharmaceutically acceptable salt thereof according to claim 14, wherein the conjugate is in a configuration of (α,α,α,α), (β,β,β,β), (α,β, β,β), (α,α,β,β), (α,α,β,β), (α,α,α,β) or a mixture thereof.

19. The PEG-naloxone conjugate or the pharmaceutically acceptable salt thereof according to claim 18, wherein the conjugate is in a configuration of (α,α,α,α).

20. The PEG-naloxone conjugate or the pharmaceutically acceptable salt thereof according to claim 18, wherein the conjugate is in a configuration of (β,β,β,β).

21. The PEG-naloxone conjugate or the pharmaceutically acceptable salt thereof according to claim 15, wherein the conjugate is selected from the group consisting of conjugates of the following structure:

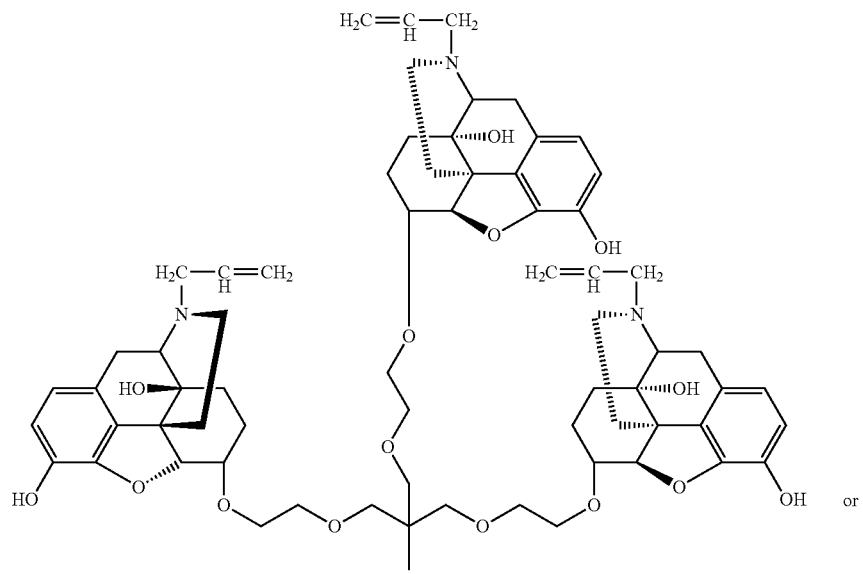
or
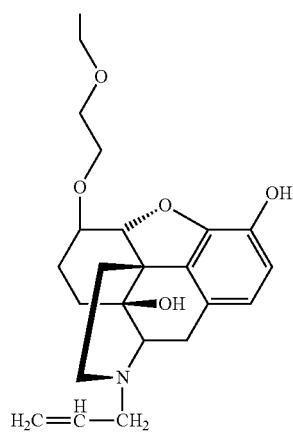
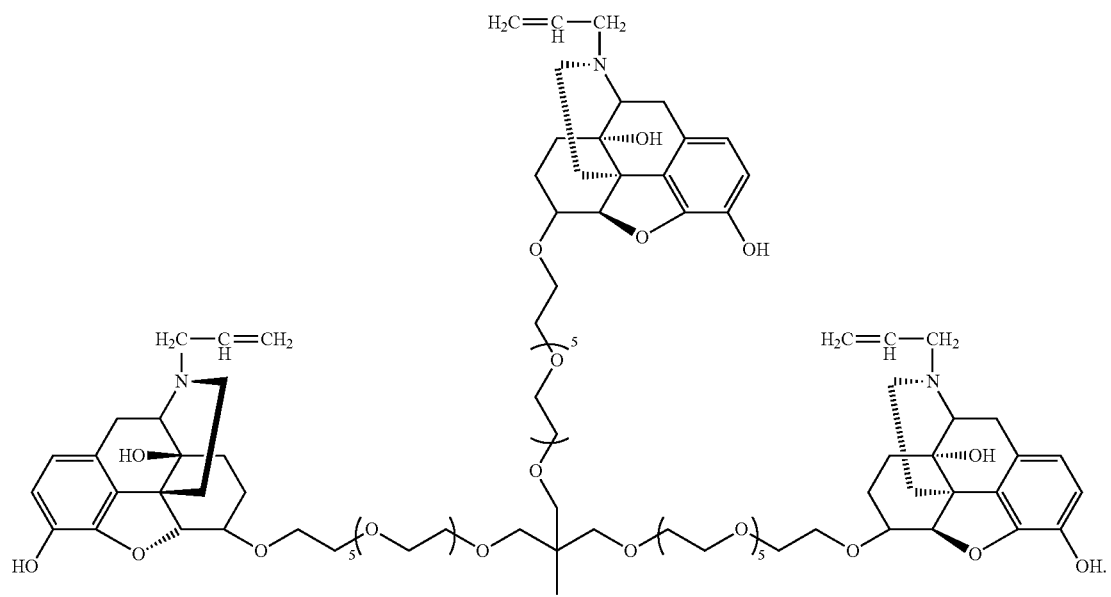

-continued

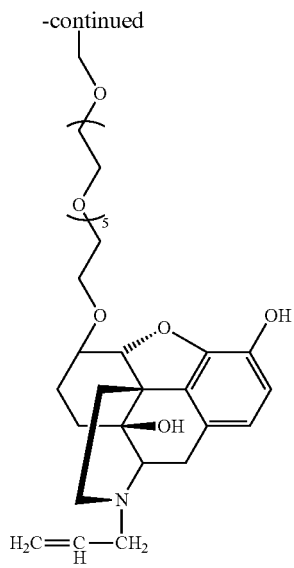

22. The PEG-naloxone conjugate or the pharmaceutically acceptable salt thereof according to claim 1, wherein the salt is selected from the group consisting of hydrochloride, hydrobromide, sulfate, nitrate, phosphate, citrate, tartrate, fumarate, maleate, lactate, benzenesulfonate, pantothenate, ascorbate salt or a combination thereof.

23. A pharmaceutical composition comprising the conjugate or the pharmaceutically acceptable salt thereof according to claim 1.

24. The pharmaceutical composition according to claim 23 in a form selected from the group consisting of tablets, injections, suppositories, pills, soft and hard gelatin capsules, powders, solutions, suspensions and aerosols.

25. A method for the treatment of bowel dysfunction and constipation caused by chronic administration of opioids comprising administering the conjugate or the pharmaceutically acceptable salt according to claim 1 to a subject in need of such treatment.

* * * * *